US005817690A

United States Patent [19]

Mewshaw

[11] Patent Number: 5,817,690

[45] Date of Patent: Oct. 6, 1998

[54] 4-AMINOETHOXY INDOLONE DERIVATIVES

[75] Inventor: Richard Eric Mewshaw, Middlesex, N.J.

[73] Assignee: American Home Products Corporation, Madison, N.J.

[21] Appl. No.: 909,800

[22] Filed: Aug. 12, 1997

Related U.S. Application Data

[60] Provisional application No. 60/024,628 filed Aug. 27, 1996.

[51] Int. Cl.[6] ........................ A61K 31/40; C07D 209/12

[52] U.S. Cl. ........................ 514/418; 514/415; 514/416; 514/307; 514/396; 548/484; 546/139

[58] Field of Search .................................. 514/418, 416, 514/307, 396; 548/484; 546/139

[56] References Cited

U.S. PATENT DOCUMENTS

| | | | |
|---|---|---|---|
| 4,314,944 | 2/1982 | Huffman et al. | 260/326.15 |
| 5,627,196 | 5/1997 | Audia et al. | 514/323 |
| 5,663,192 | 9/1997 | Bruns, Jr. et al. | 514/418 |

FOREIGN PATENT DOCUMENTS

| | | |
|---|---|---|
| 009247 | 12/1982 | Netherlands . |
| 9403425 | 2/1994 | WIPO . |

OTHER PUBLICATIONS

Corsini et al., Adv.Biochem. Psychopharmacol 16, 645–648 (1987).

Tamminga et al., Science, 200, 567–568 (1978).

Tamminga et al., Arch. Gen. Psychiatry, 43, 398–402 (1986).

Lahti et al., Mol. Pharma. 42, 432–438 (1993).

*Primary Examiner*—Richard L. Raymond
*Assistant Examiner*—Pavanaram K. Sripada
*Attorney, Agent, or Firm*—Rebecca R. Barrett

[57] ABSTRACT

A compound of the formula I:

I in which Y is hydrogen, halogen or lower alkoxy; $R_1$ is hydrogen, lower alkyl or aryl(lower)alkyl; $R_2$ is hydrogen, lower alkyl or $-(CH_2)_nX_pAr$, where X is oxygen or carbonyl; Ar is cycloalkyl, aryl or arylaryl, oxindolyl, benzimidazolyl, indolyl, 2-oxobenzimidazolyl or 2-thioxobenzimidazolyl; or $R_1$ and $R_2$, taken together with the nitrogen atom to which they are attached, complete a 3,4-dihydro-1H-isoquinolinyl or 1,3-dihydro-isoindolyl; n is one of the integers 1,2,3,4,5 or 6; p is one of the integers 0 or 1; or a pharmaceutically acceptable salt thereof are inhibitors of dopamine synthesis and release, useful in the treatment of schizophrenia, Parkinson's Disease, Tourette's Syndrome, alcohol addiction, cocaine addiction, and addiction to analogous drugs.

32 Claims, No Drawings

4-AMINOETHOXY INDOLONE DERIVATIVES

BACKGROUND OF THE INVENTION

This application claims the benefit of U.S. Provisional application Ser. No. 60/024,628 filed Aug. 27, 1996.

Efforts to induce antipsychotic activity with dopamine autoreceptor agonists have been successful [Dorsini et al., Adv. Biochem. Psychopharmacol 16, 645–648 (1977); Tamminga et al., Science 200, 567–568 (1975) and Tamminga et al., Psychiatry, 398–402 (1986)]. A method for determining intrinsic activity at the dopamine D2 receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

U.S. Pat. No. 4,314,944 to Huffman and Wilson describes a series of indolones which are useful for cardiovascular abnormalities. NL-009247 describes a series of 2-hydroxy-3-aminopropoxy)oxindoles which are useful as b-adrenergic blocking agents for the treatment of heart diseases and WO 9403425 discloses a series of heterocyclic derivatives useful in the treatment of cardiovascular diseases.

DESCRIPTION OF THE INVENTION

In accordance with this invention, there is provided a group of aminoethoxy indolone derivatives which are useful antipsychotic agents. In addition, this invention provides processes for preparation of the compounds and methods for their use in treating diseases of the central nervous system. The aminoethoxy indolone derivatives of this invention are illustrated by the following Formula I:

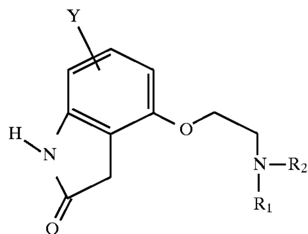

The compounds of this invention are dopamine agonists with various degrees of intrinsic activity. Some are selective autoreceptor agonists and others bind to the postsynaptic $D_2$ receptors. The autoreceptor agonists act as partial agonists (i.e. activate only autoreceptors versus postsynaptic $D_2$ dopamine receptors). As such, they provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia. Activation of the dopamine autoreceptors results in reduced neuronal firing as well as inhibition of dopamine synthesis and release and therefore provide a means of controlling hyperactivity of the dopaminergic systems with essentially no extrapyramidal side effects (EPS).

The compounds of this invention, by virtue of their high intrinsic activity, behave as natural neurotransmitters i.e. as full agonists. As such, they are useful in the treatment of diseases having abnormal concentrations of dopamine and can be used as dopamine surrogates in the treatment of Parkinson's disease.

More specifically, the compounds of this invention are 4-aminoethoxy-1,3-dihydro-indol-2-ones and derivatives which are illustrated by Formula I.

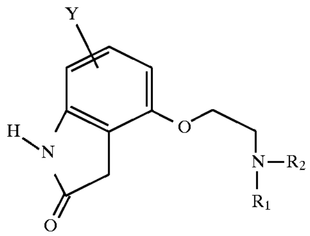

in which:

Y is hydrogen, halogen or alkoxy of 1 to 6 carbon atoms;

$R_1$ is hydrogen, alkyl of 1 to 6 carbon atoms or arylalkyl of 7 to 12 carbon atoms;

$R_2$ is hydrogen, alkyl of 1 to 6 carbon atoms or —$(CH_2)_nX_pAr$, where

X is oxygen or carbonyl;

Ar is cycloalkyl of 5 to 7 carbon atoms, aryl of 6 to 12 carbon atoms, haloaryl of 6 to 12 carbon atoms or arylaryl of 12 to 16 carbon atoms, oxindolyl, benzimidazolyl, indolyl, 2-oxobenzimidazolyl or 2-thioxobenzimidazolyl;

or $R_1$ and $R_2$, taken together with the nitrogen atom to which they are attached, complete a 3,4-dihydro-1H-isoquinolinyl or 1,3-dihydro-isoindolyl moiety;

n is one of the integers 1,2,3,4,5 or 6;

p is one of the integers 0 or 1;

or a pharmaceutically acceptable salt thereof.

A more preferred group of compounds are those in which Y is hydrogen, chlorine, fluorine or alkyl of 1 to 3 carbon atoms; $R_1$ is hydrogen, alkyl of 1 to 3 carbon atoms or arylalkyl of 7 to 8 carbon atoms; $R_2$ is hydrogen, alkyl of 1 to 3 carbon atoms or —$(CH_2)_nX_pAr$, where X is carbonyl, Ar is cycloalkyl of 5 to 7 carbon atoms, aryl of 6 to 12 carbon atoms, haloaryl of 6 to 12 carbon atoms, biphenyl, oxindolyl or indolyl; or $R_1$ and $R_2$ taken together with the nitrogen atom to which they are attached, complete a 3,4-dihydro-1H-isoquinolinyl or 1,3-dihydro-isoindolyl moiety; n is one of the integers 1,2,3 or 4; p is 0 or 1; or a pharmaceutically acceptable salt thereof.

The compounds of this Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzenesulfonic hydrochloric hydrobromic, sulfuric, cyclohexylsulfamic, phosphoric and nitric acids.

The compounds of Formula I are generally prepared by the overall sequence indicated in Schemes I–IV as follows:

Scheme I
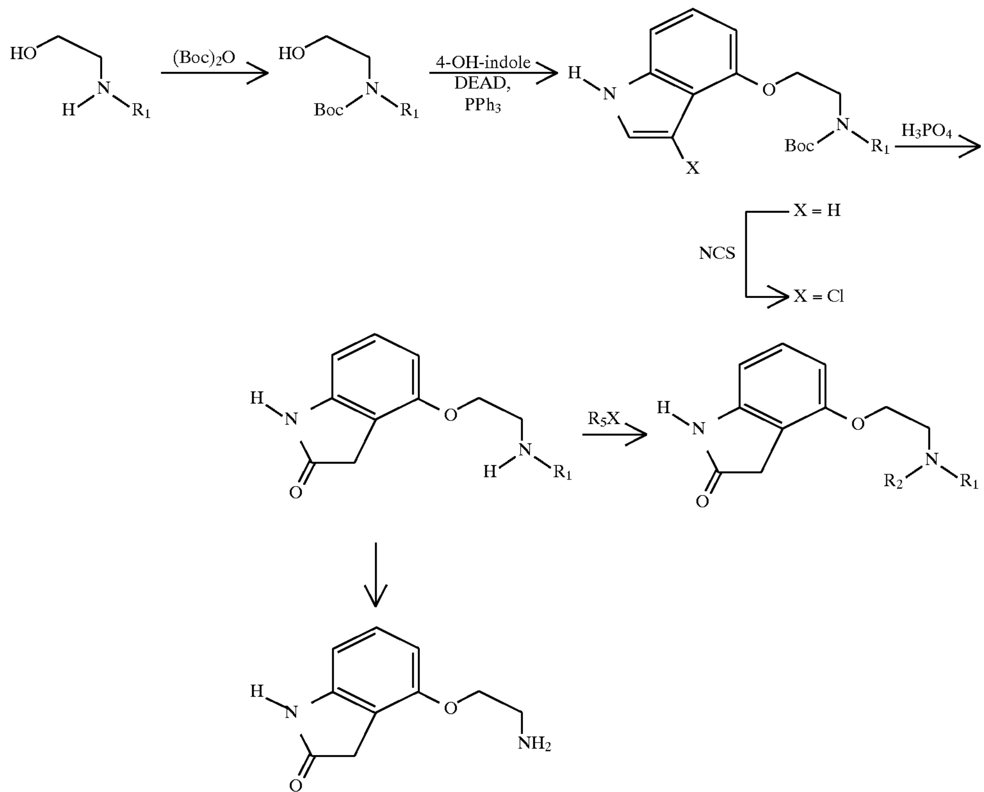
Scheme II
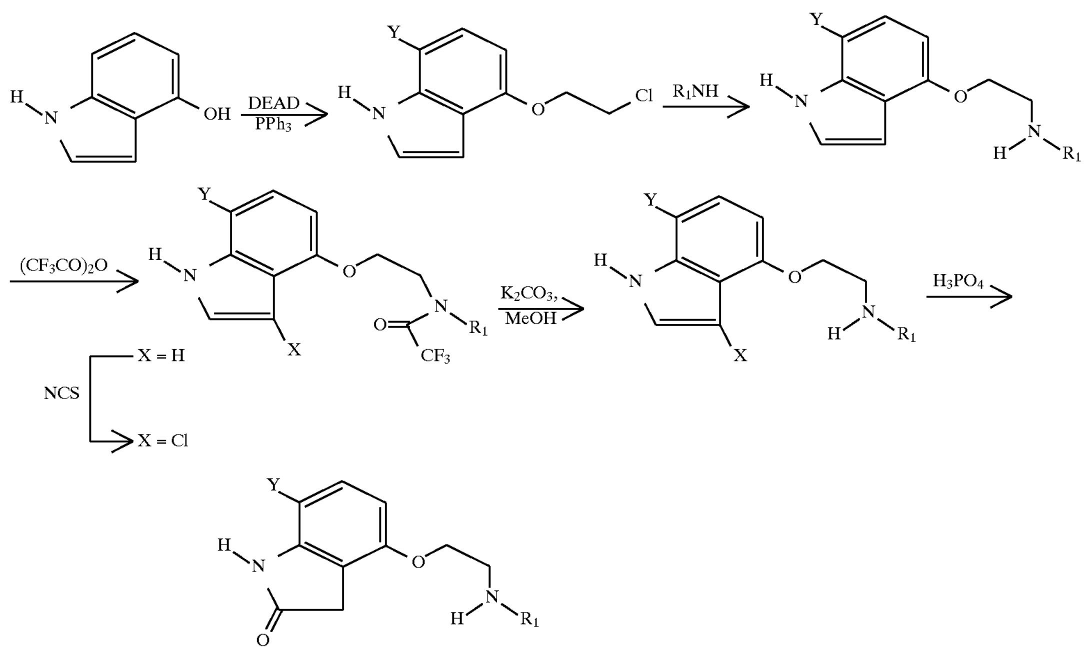

Scheme III
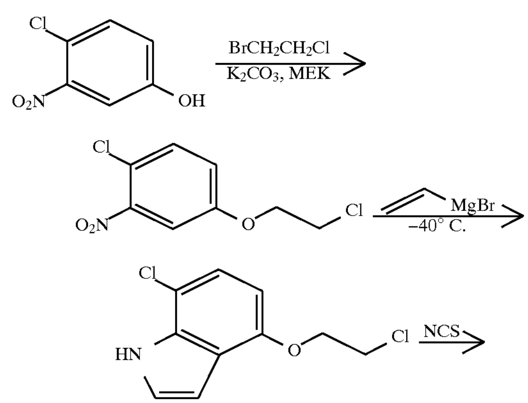
-continued
Scheme III
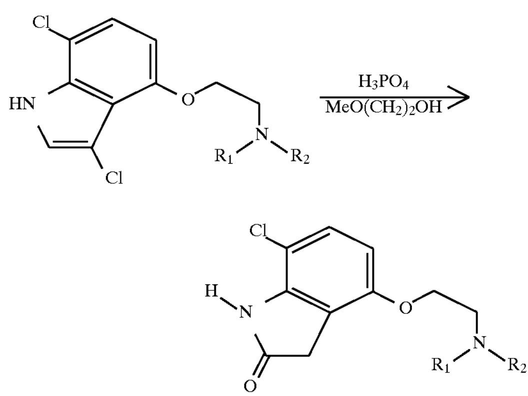
Scheme IV
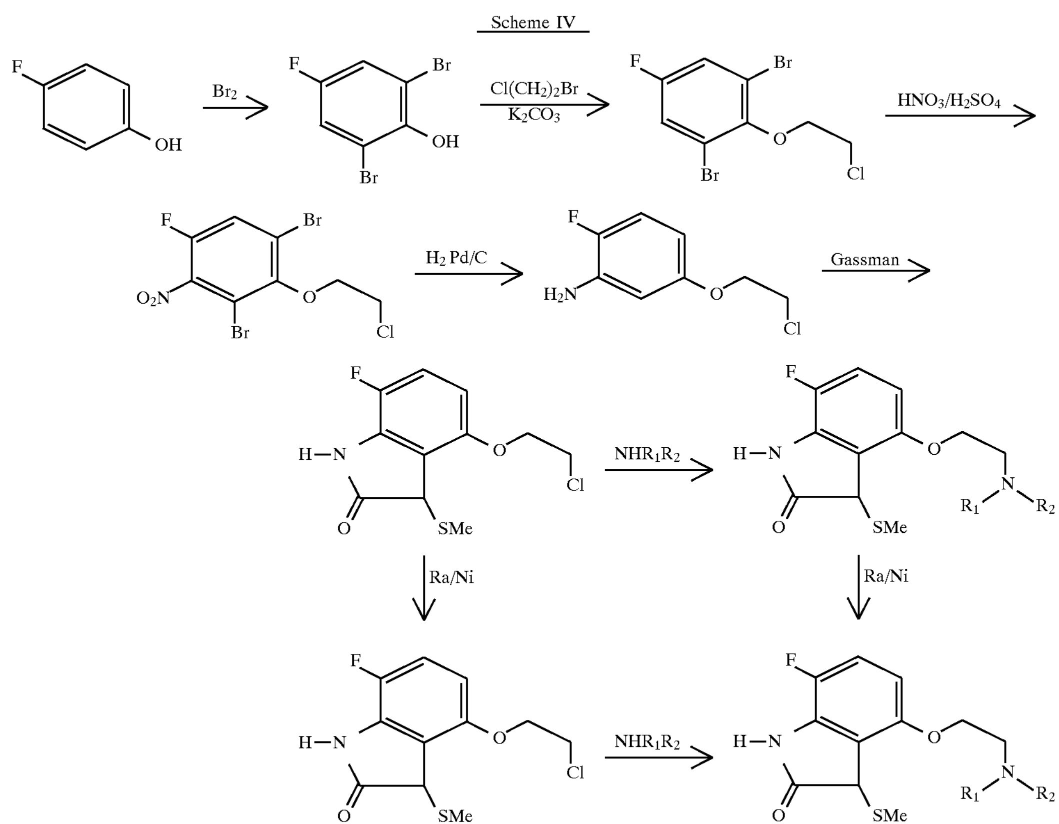
-continued
Scheme III
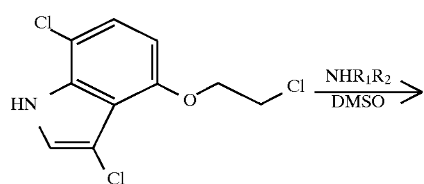

SCHEME V

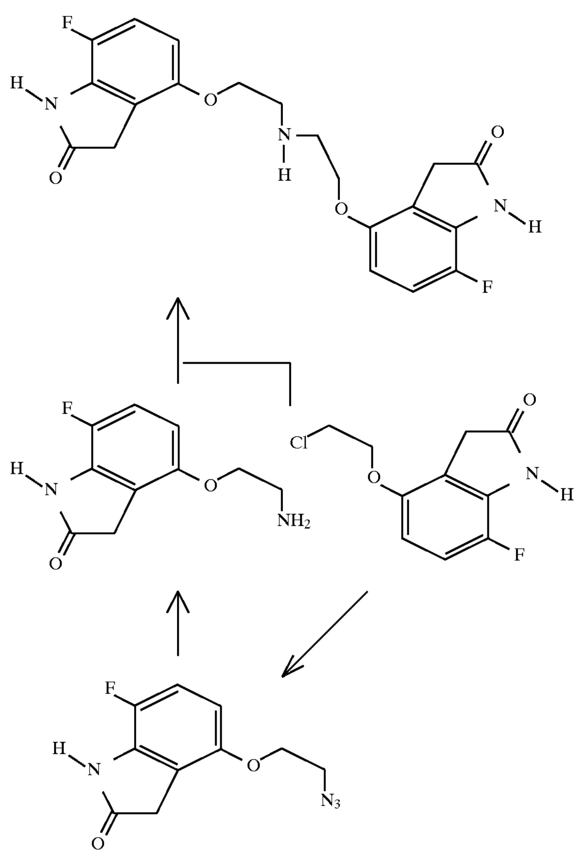

The following examples of the compounds of this invention and their production are presented by way of illustration rather than limitation on the true scope of the invention.

Intermediate 1

N-Benzyl-N-(2-hydroxy-ethyl)-carbamic acid tert-butyl ester

A solution of N-benzylaminoethanol (4.8 g, 31.9 mmol) and di-tertbutyl-dicarbonate (7.5 g, 34.4 mmol) in anhydrous tetrahydrofuran (30 mL) was stirred at ambient temperature for 18 hours. The solvent was removed and the product purified by flash chromatography (ethyl acetate-hexane, 1:1) to afford 8.0 g (99%) of a thick oil:

MS EI m/e 251 ($M^+$); IR (film) 1675, 1690 $cm^{-1}$; $^1H$ NMR ($CDCl_3$) δ 1.47 (9H, s), 2.44 (bs, 1H, OH), 3.39 (2H, bs), 3.70 (2H, bs), 4.48 (2H, bs), 7.22–7.35 (5H, m).

Elemental analysis for $C_{21}H_{27}NO_4$ Calc'd: C, 66.91; H, 8.42; N, 5.57 Found: C, 66.64; H, 8.59; N, 5.60

This general procedure utilizing N-methylaminoethanol afforded: (1b) N-Methyl-N-(2-hydroxy-ethyl)-carbamic acid tert-butyl ester as a clear oil (83.7%); MS m/e 175 (M+); $^1H$ NMR ($CDCl_3$) δ 1.37 (9H, s), 2.49 (3H, bs), 3.18 (2H, appt, J=6.0 Hz), 3.44 (2H, app q, J=11.6, 5.7 Hz), 4.64 (1H, bs, OH).

Elemental analysis for $C_8H_{17}NO_3$ Calc'd: C, 54.84; H, 9.78; N, 7.99 Found: C, 54.35; H, 10.00; N, 7.84

Intermediate 2

N-Benzyl-N-[2-(1H-indol-4-yloxy)-ethyl]-carbamic acid tert-butyl ester

To a solution of N-benzyl-N-(2-hydroxy-ethyl)-carbamic acid tert-butyl ester (12.7 g, 50.5 mmol), 4-hydroxyindole (4.5 g, 33.6 mmol) and triphenylphosphine (14.1 g, 53.8 mmol) in anhydrous tetrahydrofuran (130 mL) was slowly added a solution of diethylazidocarboxylate (9.38 g, 53.8 mmol) in tetrahydrofuran (15 mL) at room temperature. The reaction was allowed to stir for 16 hours then the solvent was removed and the crude product dissolved in diethyl ether and diluted with hexanes. After standing for 30 minutes, the solid was filtered and the filtrate concentrated. The product was purified by flash chromatography to afford 8.6 g of a yellow oil (69.7%).

Elemental analysis for $C_{22}H_{26}N_2O_3$ Calc'd: C, 72.11; H, 7.15; N, 7.64 Found: C, 71.39; H, 7.28; N, 7.21

This general procedure utilizing N-methyl-N-(2-hydroxy-ethyl)-carbamic acid tert-butyl ester or 2-chloroethanol afforded, respectively:

(2b) N-Methyl-N-[2-(1H-indol-4-yloxy)-ethyl]-carbamic acid tert-butyl ester as a yellow oil; (77.2%); MS EI m/e 290 ($M^+$).

(2c) 2-(1H-Indol-4-yloxy)-chloroethane: (57%), mp 62°–63° C.; $^1H$ NMR ($CDCl_3$) δ 3.88 (2H, t, J=6.2 Hz), 4.38 (2H, t, J=6.2 Hz), 6.52 (1H, d, J=7.3 Hz), 6.68 (1H, app. t, J=2.2 Hz), 7.02–7.12 (3H, m), 8.14 (1H, s).

Intermediate 3

N-Benzyl-N-[2-(3-chloro-1H-indol-4-yloxy)-ethyl]-carbamic acid tert-butyl ester

To a solution of N-benzyl-N-[2-(1H-indol-4-yloxy)-ethyl]-carbamic acid tert-butyl ester (6.3 g, 17.2 mmol) in tetrahydrofuran (100 mL) was added N-chlorosuccinimide (2.3 g, 17.2 mmol) in two portions over 1 hour. The reaction was allowed to stir for 18 hours and the solvent was removed under vacuum. The mixture was dissolved in diethyl ether and the insoluble solids filtered. The solvent was again removed and the product purified by chromatography (30% ethyl acetate-hexanes) to afford 5.65 g of white solid (81.9%): mp 114°–116° C.

Elemental analysis for $C_{22}H_{25}N_2O_3Cl$ Calc'd: C, 65.91; H, 6.28; N, 6.99 Found: C, 65.61; H, 6.21; N, 6.89

This general procedure utilizing N-methyl-N-[2-(1H-indol-4-yloxy)-ethyl]-carbamic acid tert-butyl ester or 7-chloro-4-(2-chloroethoxy)-1H-indole (Intermediate 5, infra) afforded, respectively:

(3b) N-Methyl-N-[2-(3-chloro-1H-indol-4-yloxy)-ethyl]-carbamic acid tert-butyl ester as a white solid: 74.9% yield; mp 153°–154° C.; MS FAB m/z 325 ($M^++H^+$).

Elemental analysis for $C_{16}H_{21}N_2O_3Cl$ Calc'd C, 59.17; H, 6.52; N, 8.62 Found C, 59.08; H, 6.33; N, 8.49

(3c) 3,7-Dichloro-4-(2-chloroethoxy)-1H-indole as a yellow white solid: 78.4% yield; mp 106°–107.5° C.; IR (KBr) 3400 cm−1(s, NH); $^1H$ NMR ($CDCl_3$) δ 3.91 (2H, t, J=6.2 Hz), 4.33 (2H, t, J=6.2 Hz), 6.47 (1H, d, J=8.4 Hz), 7.08–7.13 (2H, m), 8.26 (1H, bs, NH).

Elemental analysis for $C_{10}H_8NOCl_3$ Calc'd: C, 45.40; H, 3.05; N, 5.29 Found: C, 45.21; H, 2.77; N, 5.18

EXAMPLE 1

4-(2-Benzylaminoethoxy)-1,3-dihydro-indol-2-one

A mixture of N-benzyl-N-[2-(3-chloro-1H-indol-4-yloxy)-ethyl]-carbamic acid tert-butyl ester (5.4 g, 13.5 mmol) in methoxyethanol (25 mL) containing 85% phosphoic acid (10 mL) was heated to 100° C. for 1 hour. The reaction was allowed to cool and then basified with 2N sodium hydroxide and extracted with methylene chloride (2×150 mL). The organic layer dried over anhydrous magnesium sulfate, filtered and chromatographed (5% methanol-methylene chloride) to afford 3.28 g of a grayish-white solid (86.1%): mp 145°–146° C. The fumarate salt was prepared in isopropanol: mp 220°–221° C.

Elemental analysis for $C_{17}H_{18}N_2O_2.C_4H_4O_4$ Calc'd: C, 63.31; H, 5.57; N, 7.03 Found: C, 63.04; H, 5.36; N, 7.02

EXAMPLE 2

4-(2-Methylamino-ethoxy)-1,3-dihydro-indol-2-one

In the same manner as described in Example 1, the title compound was prepared from Intermediate (3b) as a grayish white solid: (65.6%), mp 153°–156° C.; MS EI m/e 206 (M+). The fumarate salt was prepared in isopropanol: mp 212°–214° C.

Elemental analysis for $C_{11}H_{14}N_2O_2$C.C4H4O4 Calc'd; C, 55.90; H, 5.63; N, 8.69 Found: C, 55.59; H, 5.58; N, 8.50

EXAMPLE 3

4-(2-Amino-ethoxy)-1,3-dihydro-indol-2-one

A mixture of 4-(2-benzylaminoethoxy)-1,3-dihydro-indol-2-one (1.93 g, 6.84 mmol) in absolute ethanol (50 mL) containing 10% palladium on carbon (400 mg) was shaken in a Parr hydrogenator for 4 days at room temperature. The catalyst was filtered and washed with methanol. The solvent was removed under vacuum to afford a light tan solid (1.15 g, 87.5%): mp 146°–148° C.; MS EI m/e 192 ($M^+$): HRMS for $C_{10}H_{12}N_2O_2$ calc 192.089878, found 192.0845365.

Elemental analysis for $C_{10}H_{12}N_2O_2$ Calc'd: C, 62.49; H, 6.29; N, 14.57 Found: C, 62.23; H, 6.23; N, 14.16

Intermediate 4

1-(2-Chloroethoxy)-4-chloro-3-nitrobenzene

To a 500 mL 3-neck round-bottom flask was added 4-chloro-3-nitro-phenol (10 g, 0.058 mol), potassium carbonate (20 g, 0.14 mol), bromochloroethane (34.5 g, 0.24 mol) and 2-butanone (200 mL). The mixture was mechanically stirred and heated to reflux for 20 hours under nitrogen then allowed to cool to room temperature and the solids were filtered. The solvent was evaporated under vacuum and the oil dissolved in diethyl ether (300 mL) and washed with 10% sodium hydroxide. The organic layer was dried over anhydrous magnesium sulfate, filtered and the solvent removed under vacuum. The product was dissolved in 1:1 methylene chloride-hexanes and filtered through a short pad silica. Upon concentration and standing 12.9 g (94.8.% %) of light yellow crystalline solid was afforded: mp 46°–48° C.; MS EI m/e 235, 237, 239 ($M^+$); $^1$H NMR (400 MHz, DMSO-$d_6$) δ 3.95 (t, 2H, J=5.2 Hz), 4.36 (t, 2H, J=5.2 Hz), 7.32 (dd, 1H, J=3.2, J=8.9 Hz), 7.66, (d, 1H, J=9 Hz), 7.69, (d, 1H, J=3.2 Hz).

Elemental analysis for $C_8H_7Cl_2NO_3$ Calc'd: C, 40.71; H, 2.99; N, 5.93 Found: C, 40.89, H, 2.70; N, 5.83

Intermediate 5

7-Chloro-4-(2-chloroethoxy)-1H-indole

To a solution of 1-(2-chloroethoxy)-4-chloro-3-nitrobenzene (10.00 g, 0.042 mol) in THF (230 mL) stirred in a cold bath at −50° to −40° C. was added a THF solution of vinylmagnesium bromide (132 mL, 1.0M, 0.132 mol) over 2 minutes. After stirring in the cold bath for 2–2.5 hours, saturated $NH_4Cl$ (150 mL) was added to the cold solution and it was removed from the cold bath. 1M HCl was added to dissolve the precipitated solids and the mixture was stirred for 0.5 hour. The layers were separated and the aqueous phase was extracted once with diethyl ether (80 mL). The organic layer combined and dried over anhydrous magnesium sulfate, filtered and the solvent evaporated to give 15.43 g of a dark oil. Purification by chromatography (hexanes-methylene chloride, 2:1) afforded a solid which was triturated with hexane and filtered to afford the product as yellowish white solid: 3.51 g (36%); mp 73°–75° C.; MS EI m/e 229,231, 233 ($M^+$); $^1$H NMR (400 MHz, DMSO-$d_6$) δ 3.99 (t, 2H;, J=5.1 Hz), 4.34 (t, 2H, J=5.0 Hz), 6.51 (t, 1H, J=2.7 Hz), 6.53 (d, 1H, J=7.8 Hz), 7.04 (d, 1H, J=8.0 Hz), 7.29 (t, 1H, J=2.7 Hz), 11.43 (s, 1H).

Elemental analysis for $C_{10}H_9Cl_2NO$ Calc'd: C, 52.20; H, 3.94; N, 6.09 Found: C, 52.09; H, 3.92; N, 5.96

Intermediate 6

3,7-Dichloro-4-(2-chloroethoxy)-1H-indole

To a solution of 7-chloro-4-(2-chloroethoxy)-1H-indole (4.61 g, 20.0 mmol) in acetonitrile (100 mL) was added N-chlorosuccimide (2.94 g, 2.20 mmol) at room temperature. The reaction was allowed to stir for 1.5 h then poured into water (100 mL) and extracted with methylene chloride (200 mL). The organic layer was dried over anhydrous magnesium sulfate, filtered, and the solvent removed under vacuum to afford a dark solid. This material was chromatographed (methylene chaoride-hexanes: 1:2) to afford 4.15 g (78.4%) as a white solid: mp 106°–107.5° C.; IR (KBr) 3400 cm−1; MS EI m/e 263, 265, 267, 269 (M+); $^1$H NMR ($CDCl_3$) δ 3.91 (2H, t, J=6.2 Hz), 4.33 (2H, t, J=6.2 Hz), 6.47 (1H, d, J=8.4 Hz), 7.08–7.13 (2H, m), 8.26 (1H, bs, NH).

Elemental analysis for $C_{10}H_8NOCl_3$ Calc'd: C, 45.40; H, 3.05; N, 5.30 Found: C, 44.64; H, 2.74; N, 5.16

Intermediate 7

[2-(1H-Indol-4-yloxy)-ethyl]-(4-phenyl-butyl)-amine

A solution of the 2-(1H-indol-4-yloxy)-chloroethane (1.80 g, 9.20 mmol) and 4-phenyl-1-aminobutane (4.12 g, 27.6 mmol) in anhydrous dimethylsulfoxide (25 mL) was heated to 80° C. for 6 hours. The reaction mixture was poured into water (150 mL) and extracted with methylene chloride (3×100 mL). The organic layers were combined and dried over anhydrous magnesium sulfate, filtered, and the solvent concentrated. Purification with flash chromatography (5% methanol-$CH_2Cl_2$) afforded 1.89 g (65.9%) of a tan oil: MS m/e 308 (M+). The oxalate salt was prepared in tetrahydrofuran: mp 202°–204° C.

Elemental analysis for $C_{20}H_{24}N_2O.C_2H_2O_4.0.5H_2O$ Calc'd; C, 64.85; H, 6.68; N, 6.87 Found: C, 64.66; H, 6.61; N, 6.70

This general procedure utilizing 7-chloro-4-(2-chloroethoxy)-1H-indole and 3,7-dichloro-4-(2-chloroethoxy)-1H-indole and reacting each with benzylamine afforded:

(7b) Benzyl-[2-(7-chloro-1H-indol-4-yloxy)-ethyl]-amine (68%). The fumarate salt was prepared in isopropanol as colorless crystals; mp 168°–170° C.; MS EI m/e 300/302 ($M^+$).

Elemental analysis for $C_{17}H_{17}ClN_2O.0.5\ C_4H_4O_4.0.25\ C_3H_8O$ Calc'd: C, 63.45; H, 5.66; N, 7.49 Found: C, 63.12; H, 5.61; N, 7.31

(7c) Benzyl-[2-(3,7-dichloro-1H-indol-4-yloxy)-ethyl]-amine (67.8%): mp 129°–130° C.; MS m/e 334, 336, 338 ($M^+$).

This general procedure utilizing 3,7-dichloro-4-(2-chloroethoxy)-1H-indole and reacting with 4-fluorobenzyl, 4-chlorobenzylamine, 4-methylbenzylamine, N-methylbenzylamine, n-butylamine, 1,2,3,4-tetrahydroisoquinoline, isoindoline, biphenyl-4-methylamine, and 2-naphthylmethylamine.

(7d) 4-Fluoro-benzyl-[2-(3,7-dichloro-1H-indol-4-yloxy)-ethyl]-amine (64.5%): mp 102.5°–103.5° C.; MS EI m/e 352 ($M^+$).

Elemental analysis for $C_{17}H_{15}FCl2N_2O$ Calcd: C, 57.81; H, 4.28; N, 7.93 Found: C, 57.68; H, 4.16; N, 7.86

(7e) 4-Chloro-benzyl-[2-(3,7-dichloro-1H-indol-4-yloxy)-ethyl]-amine (59.9%): mp 115°–116° C.; MS EI m/e 368 ($M^+$).

Elemental analysis for $C_{17}H_{17}H_{15}Cl_3N_2O.0.25H_2O$ Calcd: C, 54.57; H, 4.17; N, 7.49 Found: C, 54.43; H, 3.82; N, 7.32

(7f) 4-Methyl-benzyl-[2-(3,7-dichloro-1H-indol-4-yloxy)-ethyl]-amine: (88%); MS EI m/e 348 ($M^+$).

(7g) N-Methyl-N-4-methyl-benzyl-[2-(3,7-dichloro-1H-indol-4-yloxy)-ethyl]-amine: (73%); MS EI m/e 348/350/352 ($M^+$).

Elemental analysis for $C_{18}H_{18}Cl_2N_2O.0.5C_4H_4O_4 0.5H_2O$ Calcd: C, 61.90; H, 5.19; N, 8.02 Found: C, 61.46; H, 5.07; N, 7.88

(7h) Butyl-[2-(3,7-dichloro-1H-indol-4-yloxy)-ethyl]-amine (69.9%): mp 109°–111.5° C.; MS m/e 300/302/304 ($M^+$).

(7i) Tetrahydroisoquinolinyl-[2-(3,7-dichloro-1H-indol-4-yloxy)-ethyl]-amine (56% yield): MS m/e 359/361/363 ($M^+$).

(7j) Tetrahydroisoindolinyl-[2-(3,7-dichloro-1H-indol-4-yloxy)-ethyl]-amine (60%): MS m/e 345/347/349 (M+).

(7k) Biphenyl-4-methyl-[2-(3,7-dichloro-1H-indol-4-yloxy)-ethyl]-amine (36%): MS EI m/e 411/413/415 ($M^+$).

(7l) 2-Napthyl-[2-(3,7-dichloro-1H-indol-4-yloxy)-ethyl]-amine (49%): MS EI m/e 384/386/388 ($M^+$).

EXAMPLE 4

7-Chloro-4-[2-(4-fluoro-benzylamino)]-ethoxy]-1,3-dihydro-indol-2-one

In the same manner as described in Example 1, the tide compound was produced as a crystalline solid (82%), mp 148°–149.5° C.; MS EI m/e 334/336. The fumarate salt was prepared in isopropanol: mp 225°–226° C.; MS EI m/e 334 ($M^+$).

Elemental analysis for $C_{21}H_{20}N_2O_6ClF.0.25C_3H_8O.0.5H_2O$ Calc'd: C, 55.01; H, 4.88; N, 5.90 Found: C, 54.90; H, 4.64; N, 5.83

EXAMPLE 5

7-Chloro-4-[2-(4-chloro-benzylamino)]-ethoxy]-1,3-dihydro-indol-2-one

In the same manner as described in Example 1, the tide compound was produced as a crystalline solid (84.4%); mp 158°–159.5° C. The fumarate salt was prepared in ethanol: mp 217°–218° C.; MS EI m/e 350 (M+).

Elemental analysis for $C_{17}H_{16}Cl_2N_2O_2.C_4H_4O_4$ Cal'd: C, 53.97; H, 4.31; N, 5.99 Found: C, 53.78; H, 4.12; N, 5.99

EXAMPLE 6

7-Chloro-4-[2-(4-methyl-benzylamino)]-ethoxy]-1,3-dihydro-indol-2-one

In the same manner described in Example 1, the title compound was produced in 76% yield. The fumarate salt was prepared in ethanol: mp 205°–206° C.; MS EI m/e 330 (M+).

Elemental analysis for $C_{18}H_{19}ClN_2O_2.C_4H_4O_4$ Calcd: C, 59.13; H, 5.19; N, 6.27 Found: C, 58.86, H, 5.13, N, 6.58

EXAMPLE 7

4-[2-(N-Benzyl-N-methyl-amino)-ethoxy]-7-chloro-1,3dihydro-indol-2-one

In the same manner described in Example 1, the title compound was produced in 82% yield. The fumarate salt was prepared in ethanol; mp 153°–173° C.

Elemental analysis for $C_{18}H_{19}ClN_2O_2.0.5C_4H_4O_4.0.5H_2O$ Calcd: C, 60.38; H, 5.57; N, 7.04 Found: C, 60.78; H, 5.20; N, 7.03

EXAMPLE 8

4-(2-Butylamino-ethoxy)-7-chloro-1,3-dihydro-indol-2-one

In the same manner described in Example 1, the title compound was produced in 35% yield. The fumarate salt was prepared in ethanol: mp 218°–219° C.

Elemental analysis for $C_{14}H_{19}ClN_2O_2.0.5\ C_4H_4O_4$ Calcd: C, 56.39; H, 6.21; N, 8.22 Found: C, 56.11; H, 6.22; N, 7.93

EXAMPLE 9

7-Chloro-4-[2-(3,4-dihydro-1H-isoguinolin-2-yl)-ethoxy]-1,3-dihydro-indol-2-one In the same manner as described in Example 1, the title compound was produced in 38% yield. The fumarate salt was prepared in ethanol; mp 214°–216.5° C.

Elemental analysis for $C_{19}H_{19}ClN_2O_2.0.5C_4H_4O_4.0.25H_2O$ Calc'd: C, 62.22; H, 5.35; N, 6.91 Found: C, 62.27; H, 5.16; N, 6.76

EXAMPLE 10

7-Chloro-4-[2-(1,3-dihydro-isoindol-2-yl)-ethoxy]-1,3-dihydro-indol-2-one

In the same manner described in Example 1, the title compound was produced in 84% yield. The fumarate salt was prepared in ethanol; mp 220°–224° C.

Elemental analysis for $C_{18}H_{17}ClN_2O_2.C_4H_4O_4$ Calc'd: C, 59.40; H, 4.76; N, 6.30 Found: C, 59.97; H, 4.77; N, 6.51

EXAMPLE 11

4-{2-[(Biphenyl-4-ylmethyl)-amino]-ethoxy}-7-chloro-1,3-dihydro-indol-2-one

In the same manner described in Example 1, the title compound was produced in 52% yield. The fumarate salt was prepared in ethanol: mp 221°–222° C.

Elemental analysis for $C_{23}H_{21}ClN_2O_2.0.5C_4H_4O_4$ Cal'd: C, 66.59; H, 5.14; N, 6.21 Found: C, 66.35; H, 5.05; N, 6.23

EXAMPLE 12

7-Chloro-4-{2-[(napthalen-2-ylmethyl)-amino-ethoxy-1,3-dihydro-indol-2-one

In the same manner described in Example 1, the title compound was produced in 22% yield. The fumarate salt was prepared in ethanol: mp 165°–176° C.

Elemental analysis for $C_{21}H_{19}ClN_2O_2.0.7C_4H_4O_4$ Calc'd: C, 63.79; H, 4.90; N, 6.25 Found: C, 63.56; H, 4.71; N, 5.97

Intermediate 8

[2-(1H-Indol-4-yloxy)-ethyl]-(4-phenyl-butyl)-trifluoroacetylamide

To a solution of [2-(1H-indol-4-yloxy)-ethyl]-(4-phenyl-butyl)-amine (2.38 g, 7.72 mmol) and triethylamine (1.56 g, 15.4 mmol) in anhydrous methylene chloride (30 mL) at room temperature was slowly added trifluoroacetic anhydride (2.42 g, 11.6 mmol) over 10 minutes. The reaction was stirred for 1 hour then poured into a 1:1 solution of saturated sodium carbonate-water (50 mL) and extracted with methylene chloride (2×100 mL). The organic layer dried over anhydrous magnesium sulfate, filtered, and the solvent evaporated. Purification by flash chromatography (20% ethyl acetate-hexanes) afforded 1.61 g (51.6%) of an off-white solid: mp 70°–72° C.; MS m/e 404 (M+); IR (KBr) 3360, 2950, 1725 $cm^{-1}$.

This procedure utilizing N-benzyl-[2-(7-chloro-1H-indol-4-yloxy)-ethyl]-amine also afforded:

(8b) N-Benzyl-N-[2-(7-chloro-1H-indol-4-yloxy)-ethyl]-2,2,2-trifluoro-acetamide as light yellow crystals: (47%); mp 114°–116° C.; MS EI m/e 396 ($M^+$; IR (KBr) 1682 $cm-^1$; $^1H$ NMR (400 MHz, $CDCl_3$) δ 3.79 and 3.86 (2t, 2H, J=5.6 Hz, J=5.0 Hz, rotamers), 4.28 and 4.31 (2t, 2H, J=5.6 Hz, J=5.0 Hz, rotamers), 4.89 and 4.93 (2s, 2H, rotamers), 6.38 and 6.40 (2d, 1H, J=8.3 Hz, J=8.5 Hz, rotamers), 6.64–6.68 (m, 1H), 7.05 and 7.08 (2d, 1H, J=8.1 Hz, J=8.3 Hz, rotamers); 7.19–7.44 (m, 6H), 8,42 (s, 1H).

Elemental analysis for $C_{19}H_{16}N_2O_2ClF_3$ Calc'd: C, 57.51; H, 4.06; N, 7.06 Found: C, 57.11; H, 3.88; N, 7.01.

Intermediate 9

[2-(3-Chloro-1H-indol-4-yloxy)-ethyl]-(4-phenyl-butyl)-trifluoroacetylamide

To a solution of [2-(1H-indol-4-yloxy)-ethyl]-(4-phenyl-butyl)-trifluoro-acetylamide (1.55 g, 3.83 mmol) in anhydrous tetrahydrofuran (20 mL) at 5° C. was added N-chlorosuccinimide (512 mg, 3.83 mmol) in two portions over 30 minutes. After stirring for another 45 minutes, the reaction was allowed to warm to room temperature and allowed to stir for another 3 hours. The reaction mixture was poured into ethyl acetate (150 mL) and washed with water (60 mL). The organic layer dried over anhydrous magnesium sulfate, filtered, and the solvent evaporated. Purification using flash chromatography (20% ethyl acetate-hexanes) afforded 1.2 g (71.4%) of a grayish white solid: mp 113°–114° C.; MS m/e 438 (M+).

Elemental analysis for $C_{22}H_{22}N_2O_2ClF_3$ Calc'd: C, 60.21; H, 5.05; N, 6.38 Found: C, 60.51; H, 4.94; N, 6.31

This general procedure utilizing N-benzyl-N-[2-(7-chloro-1H-indol-4-yloxy)-ethyl]-2,2,2-trifluoro-acetamide also afforded:

(9b) N-Benzyl-N-[2-(3,7-dichloro-1H-indol-4-yloxy)-ethyl]-2,2,2-trifluoro-acetamide as a white solid: 82% yield; mp 156°–158° C.; MS EI m/e 430, 432, 434 ($M^+$);

IR(KBr) 1680 $cm^{-1}$; $^1H$ NMR (400 MHz, $CDCL_3$) δ 3.76 and 3.81 (2t, 2H, J=1.3 Hz, J=1.4 Hz, rotamers), 4.14 and 4.15 (2t, 2H, J=1.5 Hz, J=1.6 Hz, rotamers), 4.95 and 4.96 (2s, 2H, rotamers), 6.41 and 6.43 (2d, 1H, J=8.4 Hz, J=8.7 Hz, rotamers), 7.095 and 7.097 (2d, 1H, J=8.2 Hz, J=8.2 Hz, rotamers), 7.16 (d, 1H, J=2.5 Hz), 7.22–7.41 (m, 5H), 8.27–8.35 (m, 1H).

Elemental analysis for $C_{19}H_{15}Cl_2F_3N_2O_2$ Calcd: C, 52.92; H, 3.51; N, 6.50 Found: C, 52.54; H, 3.26; N, 6.29

Intermediate 10

[2-(3-Chloro-1H-indol-4-yloxy)-ethyl]-(4-phenyl-butyl)-amine

A mixture of [2-(3-chloro-1H-indol-4-yloxy)-ethyl]-(4-phenyl-butyl)-trifluoro-acetylamide (1.15 g, 2.62 mmol) and potassium carbonate (2.53 g, mmol) in a solution of methanol-water (50 mL:3 mL) was heated to reflux for 3 h. The solvent removed under vacuum and the crude product was dissolved in methylene chloride (150 mL) and washed with water (100 mL). The aqueous layer was extracted again with methylene chloride (100 mL) and the combined organic layers dried over anhydrous magnesium sulfate, filtered, and the solvent evaporated. The product was purified by flash chromatography (5% methanol-methylene chloride) to afford 847 mg (94.3%) of a tan oil: MS m/e 342 (M+), 344 (M+). The fumarate salt was prepared in isopropanol: mp 195°–196° C.

Elemental analysis for $C_{20}H_{23}N_2OCl.0.5C_4H_4O_4$ Calc'd: C, 65.91; H, 6.29; N, 6.99 Found: C, 66.15; H, 6.38; N, 6.81

This general procedure utilizing N-benzyl-N-[2-(3,7-dichloro-1H-indol-4-yloxy)-ethyl]-2,2,2-trifluoro-acetamide afforded:

(10b) Benzyl-[2-(3,7-dichloro-1H-indol-4-yloxy)-ethyl]-amine: (92%). The fumarate salt was prepared as a white powder; mp 201°–202° C.; MS EI m/e 334, 336, 338 ($M^{30}$ ).

Elemental analysis for $C_{17}H_{16}Cl_2N_2O.0.5C_4H_4O_4$ Calcd: C, 58.03; H, 4.61; N, 7.12 Found: C, 57.88; H, 4.45; N, 6.96

EXAMPLE 13

4-2-[4-Phenyl-butylamino)-ethoxy]-1,3-dihydro-indol-2-one

In the same manner described in Example 1, the title compound was produced as a crystalline solid (90.6%), mp 81°–83° C. The fumarate salt was prepared from isopropanol: mp 191°–193° C.; MS m/e 324 (M+).

Elemental analysis for $C_{20}H_{24}N_2O_2.C_4H_4O_4.0.1H_2O$ Calc'd: C, 65.17; H, 6.43; N, 6.33 Found: C, 64.97; H, 6.39; N, 6.25

EXAMPLE 14

4-(2-Benzylamino-ethoxy)-7-chloro-1,3-dihydro-indol-2-one

In the same manner as described in Example 1, the title compound was produced as a crystalline solid in 71% yield, mp 161°–163° C. The hemifumarate salt was prepared in ethanol: mp 199°–200° C., MS EI m/e 316, 318 ($M^{30}$ ).

Elemental analysis for $C_{17}H_{17}N_2O_2Cl.0.5C_4H_4O_4$ Calc'd: C, 60.88; H, 5.11; N, 7.47 Found: C, 60.74; H, 4.95; N, 7.37

Intermediate 11

2,6-Dibromo-4-fluorophenol

To a solution of 4-fluorophenol (25 g, 0.22. mol) in acetic acid (200 mL) at room temperature was slowly added dropwise bromine (78 g, 0.49 mol) while being mechanically stirred. After 1 h the reaction mixture was poured into ice water (1.5 L) followed by 100 mL of saturated aqueous sodium bisulfite. The solid precipitate was filtered and dried to afford 51.8 g (86.0%) a white solid: mp 54°–55° C., $^1H$ NMR ($CDCl_3$) δ 5.69 (1H, s, OH), 7.25 (2H, d, J=7.5 Hz); MS EI m/e 268/270/272 ($M^{30}$ ).

Elemental analysis for $C_6H_3Br_2FO$ Calcd: C, 26.70; H, 1.12 Found: C, 26.64; H, 1.07

Intermediate 12

1-(2-Chloroethoxy)-2,6-dibromo-4-fluorobenzene

A mixture of 2,6-dibromo-4-fluoro-phenol (55 g, 0.20 mol), potassium carbonate (60 g, 0.43 mol), 1-bromo-2-chloroethane (32.5 g, 0.23 mol) and 2-butanone (500 mL) was heated to reflux for 2 hours and allowed to cool to ambient temperature. The solids were filtered and the solvent was removed under vacuum to afford an oil. The oil was dissolved in diethyl ether (300 mL) and washed with water, dried over anhydrous magnesium sulfate, charcoalized, and filtered through Solka floc to afford 65.9 g (97.2%) of an oil; MS EI m/e 330/332/334/336 ($M^+$; $^1$H NMR ($CDCl_3$) δ 3.89 (2H, t, J=6.1 Hz), 4.23 (2H, t, J=6.1 Hz), 7.28 (2H, d, J=7.5 Hz).

Intermediate 13

1-(2-Chloroethoxy)-2,6-dibromo-4-fluoro-3-nitrobenzene

To a solution of 1-(2-chloroethoxy)-2,6-dibromo-4-fluorobenzene (65.8 g, 0.20 mol) in concentrated sulfuric acid (165 mL) maintained at room temperature using a water bath was slowly added a solution of nitric acid in sulfuric acid (10 mL $HNO_3$ in 165 mL $H_2SO_4$). The reaction was allowed to stir at room temperature for 1 hour then poured into ice (1.5 L) and extracted with methylene chloride (2×300 mL). The combined organic layers were washed with aqueous sodium bicarbonate (150 mL) and dried over anhydrous magnesium sulfate, filtered, and the solvent removed under vacuum to afford 73.3 g (97.1%) a white crystalline solid: mp 56°–57° C.; MS EI m/e 375/377/379/381; $^1$H NMR ($CDCl_3$) δ 3.91 (2H, t, J=5.9 Hz), 4.29 (2H, d, J=5.9 Hz), 7.54 (8.1 Hz).

Elemental analysis for $C_8H_5Br_2ClFNO_3$ Calcd: C, 25.46; H, 1.34; N, 3.71 Found: C, 25.46; H, 1.20; N, 3.51

Intermediate 14

1-(2-Chloroethoxy)-4-fluoro-3-aminobenzene

A solution of 1-(2-chloroethoxy)-2,6-dibromo-4-fluoro-3-nitrobenzene (73.2 g, 0.19 mol) in ethanol (1.1 L) containing 7.3 g of 10% palladium on carbon was hydrogenated at 40 psi for 5 days. The catalyst was filtered and the solvent was removed. The residue was dissolved in diethyl ether (300 mL) and washed with saturated aqueous sodium carbonate (200 mL). The organic layer separated and washed with water, dried over anhydrous magnesium sulfate, filtered, and the solvent removed to afford an oil which solidies to afford 32.5 g (90.0%) a dark solid: mp 42°–43° C.; MS EI m/e 189/191 ($M^+$); 1H NMR ($CDCl_3$) δ 3.40–3.60 (2H, bs, $NH_2$), 3.77 (2H, d, J=6 Hz), 4.14 (2H, d, J=6 Hz), 6.19–6.23 (1H, m), 6.36 (1H, dd, J=7, 3 Hz), 6.88 (1H, dd, J=11, 9 Hz).

Elemental analysis for $C_8H_9ClFNO$ Calcd: C, 50.68; H, 4.78; N, 7.39 Found: C, 50.46; H, 4.66; N, 7.46

Intermediate 15

4-(2-Chloroethoxy)-7-fluoro-3-thiomethyl-1,3-dihydro-indol-2-one

To a solution of ethyl(methylthio)acetate (7.2 g, 53.4 mmol) in anhydrous methylene chloride (200 mL) at −78° C. was added sulfuryl chloride (8.1 g, 59.7 mmol) and stirred for 20 minutes. A solution of 1-(2-chloroethoxy)-4-fluoro-3-aminobenzene (10.0 g, 52.8 mmol) and Proton Sponge (13.9 g) in methylene chloride (100 mL) was added dropwise and stirred for 2 hours, followed by the addition of triethylamine (6.5 g, 64.5 mmol). The temperature was maintained at −78° C. and the reaction mixture was allowed to stir for 1 hour. After warming to room temperature, the mixture was poured into brine (200 mL) and dried over anhydrous magnesium sulfate, filtered, and the solvent removed to afford an oil. Acetic acid (75 mL) was added to the oil and the mixture allowed to stand for 18 hours then the solvent was removed under vacuum. The residue was partitioned between diethyl ether (400 mL) and 2.5 N aqueous hydrochloric acid (150 mL). The organic layer was separated and dried over anhydrous magnesium sulfate, filtered, and the solvent removed to afford a solid. Trituration of the solid with a small amount of diethyl ether (30 mL) afforded 8.8 g (60.5%) a yellow solid: mp 140°–141° C.; MS EI m/e 275/277 ($M^+$); $^1$NMR ($CDCl_3$) δ 2.14 (3H, s), 3.79–3.87 (2H, m), 4.25–4.33 (2H, m), 4.35 (1H, s), 6.51 (1H, dd, J=9.1, 3.3 Hz), 6.99 (1H, app. t, J=9.1 Hz), 8.09 (1H, s).

Elemental analysis for $C_{11}H_{11}ClFNO_2S$ Calcd: C, 47.92; H, 4.02; N, 5.08 Found: C, 47.67; H, 3.85; N, 4.85

Intermediate 16

4-(2-Benzyl-(aminoethoxy)-7-fluoro-3-thiomethyl-1,3-dihydro-indol-2-one

The tide compound was prepared from 4-(2-chloroethoxy)-7-fluoro-3-thiomethyl-1,3-dihydro-indol-2-one (1.5 g, 5.44 mmol) and benzylamine (2.33 g, 21.8 mmol) in dimethylsulfoxide (8 mL) according to the procedure used to prepare intermediate 6 to afford 1.14 g (61%) of a yellow oil: MS EI m/e 346 ($M^+$): 1H NMR ($CDCl_3$) δ 1.96 (3H, s), 2.96–3.13 (2H, m), 3.89 (2H, m), 3.89 (2H, AB, J=13 Hz), 4.10–4.21 (2H, m), 4.28 (1H, s), 6.46 (1H, dd, J=9, 3 Hz), 6.95 (1H, app t, J=9 Hz)7.21–7.40 (5H, m).

Utilizing this general procedure and replacing benzylamine with cyclohexylmethylamine, and biphenyl-3-methylamine and 3-(1H-indol-3-yl)propylamine afforded:

(16b) 4-(2-Cyclohexylmethyl-(aminoethoxy)-7-fluoro-3-thiomethyl-1,3-dihydro-indol-2-one (48% yield); MS EI m/e 352 ($M^+$).

(16c) 4-[(2-(Biphenyl-3-methylamino)-ethoxy]-7-fluoro-3-thiomethyl-1,3-dihydro-indol-2-one (61%): MS EI m/e 422 ($M^+$).

(16d) 4-{2-[3-(1H-Indol-yl)-propylamino]-ethoxy}-7-fluoro-3-thiomethyl-1,3-dihydro-indol-2-one (64%).

EXAMPLE 15

4-(2-Benzylamino-ethoxy)-7-fluoro-1,3-dihydro-indol-2-one

To a solution of 4-(2-benzyl-(aminoethoxy)-7-fluoro-3-thiomethyl-1,3-dihydro-indol-2-one (1.05 g, 3.04 mmol) in ethanol (50 mL) was added 2 teaspoons of Raney nickel at room temperature. After 2 hours the catalyst was filtered and the solvent removed and the solid dissolved in a minimum amount of a solution of methanol in methylene chloride and passed through a silica gel column (5% methanol in methylene chloride) to afford 590 mg (65%) a pale yellow solid; mp 162°–163° C.; MS EI m/e 300 ($M^+$); $^1$H NMR (DMSO-$d_6$) δ 2.80 (2H, t, J=6 Hz), 3.42 (2H, s), 3.74 (2H, s), 4.03 (2H, t, J=6 Hz), 6.54 (1H, d, J=9, 3 Hz), 7.01 (1H, app t, J=9 Hz)7.18–7.34 H, m), 10.81 (1H, d, J=10 Hz). The fumarate salt was prepared in ethanol to afford a yellow solid: mp 202°–203° C.

Elemental analysis for $C_{17}H_{17}FN_2O_2$.0.5 $C_2H_4O_4$.0.25$H_2O$ Calc'd: C, 62.89; H, 5.42; N, 7.72 Found: C, 63.00; H, 5.34; N, 7.80

EXAMPLE 16

4-[2-(Cyclohexylmethyl-amino)-ethoxy)-7-fluoro-1,3-dihydro-indol-2one

In the same manner as described in Example 15, the title compound was produced as a light brown crystal (28%); mp 215°–216° C.

Elemental analysis for $C_{17}H_{23}FN_2O_2$.0.5 $C_4H_4O_4$ Calc'd: C, 62.81; H, 5.36; N, 6.92 Found: C, 62.18; H, 5.81; N, 5.19

EXAMPLE 17

4-{2-[(Biphenyl-3-ylmethyl)-amino]-ethoxy}-7-fluoro-1,3-dihydro-indol-2-one

In the same manner as described in Example 15, the title compound was prepared in 29% yield. The fumarate salt was prepared in ethanol: mp 200°–201° C.

Elemental analysis for $C_{23}H_{21}FN_2O_2$.$C_4H_4O_4$ Calc'd: C, 65.85; H, 5.12; N, 5.69 Found: C, 65.43 H, 5.19; N, 5.72

EXAMPLE 18

4-{2-[3-(1H-Indol-yl)-propylamino]-ethoxy-}-7-fluoro-1,3-dihydro-indol-2-one

In the same manner as described in Example 15, the title compound was prepared in 19% yield. The fumarate salt was prepared in ethanol: mp 189°–190° C.

Elemental analysis for $C_{21}H_{22}FN_3O_2$.$C_4H_4O_4$ Calc'd: C, 62.11; H, 5.42; N, 8.69 Found: C, 62.16; H, 5.45; N, 8.59

Intermediate 17

4-(2-Chloroethoxy)-7-fluoro-1,3-dihydro-indol-2-one

To a solution of 4-(2-chloroethoxy)-7-fluoro-3-thiomethyl-1,3-dihydro-indol-2-one (5.0 g, 18.1 mmol) in formic acid (75 mL) was added Raney nickel (10 g) and stirred at room temperature for 6 hours. The reaction mixture was diluted with diethyl ether (150 mL) and the catalyst filtered through celite and upon addition of water a precipitate formed. The solid was filtered and air dried to afford 1.3 g of product. The ether layer dried over magnesium sulfate, filtered, and the solvent removed under vacuum to afford another 1.5 g of product. Total yield: 2.8 g (67.4%): mp 192°–193 ° C.; MS EI m/e 229/231 ($M^+$); $^1H$ NMR ($CDCl_3$) δ 3.53 (2H, s), 3.80 (2H, t, J=5.7 Hz), 4.25 (2H, J=5.7 Hz), 6.46 (1H, dd, J=3.3, 9.2 Hz), 6.93(1H, app t, J=9.2 Hz), 7.70 (1H, bs).

EXAMPLE 19

4-[2-(1,3-Dihydro-isoindol-2-yl)-ethoxy]-7-fluoro-1,3-dihydro-indol-2-one 4-(2-Chloroethoxy)-7-fluoro-1,3-dihydro-indol-2-one was reacted with isoindoline in the same manner described for intermediate 16 to afford the title compound in 75% yield as a thick oil. The fumarate salt was prepared in ethanol: mp 210°–212° C.

Elemental analysis for $C_{18}H_{17}FN_2O_2$.$C_4H_4O_4$.0.25$C_4H_8O$ Calc'd: C, 61.88; H, 5.19; N, 6.27 Found: C, 61.33; H, 4.98; N, 6.22

EXAMPLE 20

4-{2-[(Biphenyl-4-ylmethyl)-amino]-ethoxy}-7-fluoro-1,3-dihydro-indol-2-one 4-(2-Chloroethoxy)-7-fluoro-1,3-dihydro-indol-2-one was reacted with biphenyl-2-methylamine in the same manner described for intermediate 16 to afford the title compound in 42% yield. The fumarate salt was prepared in ethanol: mp 193°–198° C.

Elemental analysis for $C_{23}H_{21}FN_2O_2$.$C_4H_4O_4$ Calc'd: C, 65.85; H, 5.12; N, 5.69 Found: C, 65.68 H, 5.03; N, 5.64

EXAMPLE 21

7-Fluoro-4-{2-[(nanthalen-2-ylmethyl)-amino]-ethoxy}-1,3-dihydro-indol-2-one 4-(2-Chloroethoxy)-7-fluoro-1,3-dihydro-indol-2-one was reacted with 2-napthyl-methylamine in the same manner described for intermediate 16 to afford the title compound in 82%yield. The fumarate salt was prepared in ethanol: mp 189°–193° C.

Elemental analysis for $C_{21}H_{19}FN_2O_2$.$C_4H_4O_4$ Cal'd: C, 64.37; H, 4.97; N, 6.01 Found: C, 64.11; H, 5.05; N, 5.72

EXAMPLE 22

4-[2-(3,4-Dihydro-1H-isoquinolin-2-yl)-ethoxy]-7-fluoro-1,3-dihydro-indol-2-one 4-(2-Chloroethoxy)-7-fluoro-1,3-dihydro-indol-2-one was reacted with dihydroisoquinoline in anhydrous dimethyl sulfoxide in the same manner described for intermediate 16 to afford the title compound in 45% yield. The fumarate salt was made in ethanol: mp 230°–235° C.

Elemental analysis for $C_{19}H_{19}FN_2O_2$.0.5 $C_4H_4O_4$.0.25$H_2O$ Calc'd: C, 64.85; H, 5.57; N, 7.20 Found: C, 64.80; H, 5.41; N, 7.29

Intermediate 18

4-(2-Azidoethoxy)-7-fluoro-1,3-dihydro-indol-2-one

A solution of 4-(2-chloroethoxy)-7-fluoro-1,3-dihydro-indol-2-one (2.04 g, 8.88 mmol) and sodium azide in dimethylformamide (125 mL) was heated to 70° C. for 18 hours. The reaction mixture was partitioned between methylene chloride (100 mL) and water (100 mL). The organic layer separated and washed with water (50 mL) then dried over anhydrous magnesium sulfate, filtered, and the solvent removed under vacuum. The crude product was filtered through a pad of silica to afford a yellow solid, mp 147°–148° C. MS EI m/e 261 ($M^+$).

Elemental analysis for $C_{10}H_9N_4O_2F$ Calc'd: C, 50.85; H, 3.84; N, 23.72 Found: C, 51.09; H, 3.60; N, 23.52

EXAMPLE 23

4-(2-Amino-ethoxy)-7-fluoro-1,3-dihydro-indol-2-one

A mixture of 4-(2-azidoethoxy)-7-fluoro-1,3-dihydro-indol-2-one (1.8 g, 7.62 mmol) and 10% palladium on carbon in ehtanol (250 mL) at room temperature was hydrogenated at 54 psi for 11 hours. The catalyst was filtered through Celite and the solvent evaporated to afford 1.54 g (96.1%) of a tan solid, mp 138°–141° C; MS m/e 210 ($M^+$). The fumarate salt was prepared in ethanol, mp 218°–221° C.

Elemental analysis for $C_{10}H_{11}N_2O_2F$.0.5$C_4H_4O_4$.0.25 $H_2O$ Calc'd: C, 52.84; H, 4.99; N, 10.27 Found: C, 53.16; H, 5.03; N, 9.80

EXAMPLE 24

Bis-[2-(7-fluoro-1,3-dihydro-indol-2-one-4-yl)-ethoxy]-amine

A solution of 4-(2-chloroethoxy)-7-fluoro-1,3-dihydro-indol-2-one (1.90 g, 8.27 mmol) and 4-(2-amino-ethoxy)-7-fluoro-1.3-dihydro-indol-2-one (1,33 g, 6.33 mmol) in dimethylsulfoxide (60 mL) was heated to 100° C. for 34 hours. The majority of the solvent was evaporated off under vacuum and the crude product dissolved in methylene chloride (300 mL) containing methanol (20 mL) and washed with aqueous saturated sodium bicarbonate (100 mL). Aqueous HCl was added to pH 8 and the organic layer was separated and the aqueous layer again washed with methylene chloride (100 mL). The combined organic layers were dried over anhydrous magnesium sulfate, filtered and the solvent removed under vacuum. Purification by chromatography ($CH_2Cl_2$-methanol: 97/3) afforded 0.73 g (30%) of a yellowish tan solid, mp 226°–228° C.; MS m/e 403 ($M^+$). The fumarate salt was prepared by adding a solution of fumaric acid (2 eq) in ethanol (50 mL) to a suspension of 700 mg of free base in warm ethanol (100 mL). The mixture was allowed to stir at near reflux temperature for 20 minutes, allowed to cool to room temperature and filtered to afford g. of salt, mp 240°–241° C.

Elemental analysis for $C_{24}H_{23}N_3O_8F_2.C_2H_4O_4$ Calc'd: C, 55.49; H, 4.46; N, 8.09 Found: C, 55.44; H, 4.45; N, 7.92

EXAMPLE 25

4-[2-(Benzyl-methyl-amino)-ethoxy]-1,3-dihydro-indol-2-one

A mixture of 4-(2-methyl-(aminoethoxy)-1,3-dihydro-indol-2-one) (480 mg, 2.33 mmol), benzyl chloride (324 mg, 25.6 mmol), and potassium carbonate (676 mg, 48.9 mmol) in anhydrous dimethylformamide (10 mL) was heated to 85° C. for 2 hours then poured into water (100 mL) and extracted with ethyl acetate (2×150 mL). The organic layer was dried over anhydrous magnesium sulfate, filtered, and the solvent removed under vacuum. The product was chromatographed to afford a yellow oil (354 mg, 51.3%): MS EI m/e 296 (M+). The fumarate salt was prepared from 1.5 equivalents of fumaric acid in warm isopropanol: mp 114°–116° C.

Elemental analysis for $C_{18}H_{20}N_2O_4$.0.5 $C_2H_4O_4$.0.75 $H_2O$ Calc'd: C, 65.29; H, 6.44; N, 7.61 Found: C, 65.09; H, 6.05; N, 7.23

EXAMPLE 26

4-{2-[Bis-(3-methyl-benzyl)-amino]-ethoxy}-1,3-dihydro-indol-2-one

Utilizing 4-(2-amino-ethoxy)-1,3-dihydro-indol-2-one prepared in example 2 and reacting with 3-methylbenzyl chloride in the same manner as described for intermediate 15 above to afford the title compound as a crystalline solid in 34% yield, mp 162–164.

Elemental analysis for $C_{26}H_{30}N_2O_2$.1.5 $C_2H_2O_4$ Calc'd: C, 65.03; H, 5.84; N, 5.23 Found: C, 64.84; H, 5.81; N, 5.19

EXAMPLE 27

4-(2-{[4-(4-Fluoro-phenyl)-4-oxo-butyl]-methyl-amino}-ethoxy)-1,3-dihydro-indol-2-one A mixture of 4-(2-methyl-(aminoethoxy)-1,3-dihydro-indol-2-one (600 mg, 2.91 mmol), 2-(3-chloropropyl)-2-(4-fluorophenyl)-1,3-dioxolane (1.16 g, 4.76 mmol) and potassium carbonate (844 mg, 6.1 mmol) in anhydrous dimethylformamide (12 mL) containing potassium iodide (80 mg) was allowed to stir 12 hours at 85° C. The solvent was removed under high vacuum and the residue dissolved in methylene chloride (150 mL) and extracted with water (2×50 mL). The organic layer was dried over anhydrous magnesium sulfate, filtered and concentrated. Purification by chromatography (5% methanol-methylene chloride) afford 800 mg of a red oil: MS EI m/e 414 (M+).

The above product was dissolved in methanol (25 mL) containing 2 mL of concentrated hydrochloric acid and allowed to stir a reflux for 3 hours. The reaction mixture was allowed to cool and the solid filtered to afford a light yellow solid which was washed with methanol (5 mL) to afford 415 mg (55.1%) of product as the hydrochloride salt: mp 246°–248° C.

Elemental analysis for $C_{21}H_{23}N_2O_3F$.HCl.0.5 $H_2O$ Calc'd: C, 60.65; H, 6.06; N, 6.74 Found: C, 60.53; H, 5.86; N, 6.72

Affinity for the dopamine autoreceptor was established by a modification of the standard experimental test procedure of Seemen and Schaus, European Journal of Pharmacology 203, 105–109 (1991), wherein homogenized rat striatal brain tissue is incubated with $^3$H-quinpirole (Quin.)and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, New York (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of these studies were as follows:

| Example No. | $IC_{50}$ (nM) $D_2$ Quin. | $IC_{50}$ (nM) $D_2$ Spiper | Ratio |
|---|---|---|---|
| (1) | 0.41 | 145 | 354 |
| (2) | 4.31 | 918 | 213 |
| (3) | 13.9 | 3425 | 246 |
| (4) | 2.54 | 176 | 69 |
| (5) | 2.81 | 51.9 | 19 |
| (6) | 1.10 | 37.5 | 52 |
| (7) | 3.68 | 231 | 63 |
| (8) | 1.89 | 144.1 | 76 |
| (9) | 1.31 | 81.4 | 62 |
| (10) | 0.55 | | |
| (11) | 41.10 | | |
| (13) | 0.45 | 25 | 55 |
| (14) | 0.82 | 36 | 44 |
| (15) | 0.91 | 68.7 | 76 |
| (16) | 1.58 | 99.4 | 63 |
| (17) | 2.57 | 53.5 | 21 |
| (18) | 0.30 | | |
| (19) | 3.57 | | |
| (20) | 11.10 | | |
| (21) | 1.27 | | |
| (22) | 1.84 | | |
| (25) | 1.52 | 645 | 424 |
| (26) | 31.2 | 19297 | 619 |
| (27) | 6.22 | 346 | 57 |

Hence, the compounds of this invention effect the synthesis of the neurotransmitter dopamine and thus are useful in the treatment of dopaminergic disorders such as schizophrenia, Parkinson's disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of the formula I:

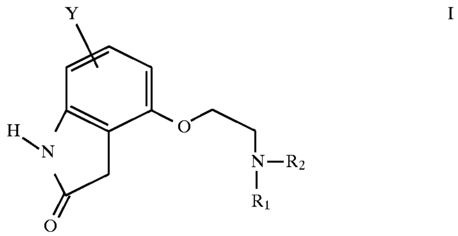

in which:

Y is hydrogen, halogen or alkoxy of 1 to 6 carbon atoms;

$R_1$ is hydrogen, alkyl of 1 to 6 carbon atoms or arylalkyl of 7 to 12 carbon atoms;

$R_2$ is hydrogen, alkyl of 1 to 6 carbon atoms or —$(CH_2)_nX_pAr$, where

X is oxygen or carbonyl;

Ar is cycloalkyl of 5 to 7 carbon atoms, aryl of 6 to 12 carbon atoms, haloaryl of 6 to 12 carbon atoms or arylaryl of 12 to 16 carbon atoms, oxindolyl, benzimidazolyl, indolyl, 2-oxobenzimidazolyl or 2-thioxobenzimidazolyl;

or $R_1$ and $R_2$, taken together with the nitrogen atom to which they are attached, complete a 3,4-dihydro-1H-isoquinolinyl or 1,3-dihydro-isoindolyl moiety;

n is one of the integers 1,2,3,4,5 or 6;

p is one of the integers 0 or 1;

or a pharmaceutically acceptable salt thereof.

2. A compound of claim 1 in which Y is hydrogen, chlorine, fluorine or alkyl of 1 to 3 carbon atoms; $R_1$ is hydrogen, alkyl of 1 to 3 carbon atoms or arylalkyl of 7 to 8 carbon atoms; $R_2$ is hydrogen, alkyl of 1 to 3 carbon atoms or —$(CH_2)_nX_pAr$, where X is carbonyl, Ar is cycloalkyl of 5 to 7 carbon atoms, aryl of 6 to 12 carbon atoms, haloaryl of 6 to 12 carbon atoms, biphenyl, oxindolyl or indolyl; or $R_1$ and $R_2$ taken together with the nitrogen atom to which they are attached, complete a 3,4-dihydro-1H-isoquinolinyl or 1,3-dihydro-isoindolyl; n is one of the integers 1,2,3 or 4; p is 0 or 1; or a pharmaceutically acceptable salt thereof.

3. The compound of claim 1 which is 4-(2-benzylaminoethoxy)-1,3-dihydro-indol-2-one or a pharmaceutically acceptable salt thereof.

4. The compound of claim 1 which 4-(2-methylamino-ethoxy)-1,3-dihydro-indol-2-one or a pharmaceutically acceptable salt thereof.

5. The compound of claim 1 which is 4-(2-amino-ethoxy)-1,3-dihydro-indol-2-one or a pharmaceutically acceptable salt thereof.

6. The compound of claim 1 which is 7-chloro-4-[2-(4-fluoro-benzylamino)]-ethoxy]-1,3-dihydro-indol-2-one or a pharmaceutically acceptable salt thereof.

7. The compound of claim 1 which is 7-chloro-4-[2-(4-chloro-benzylamino)]-ethoxy]-1,3-dihydro-indol-2-one or a pharmaceutically acceptable salt thereof.

8. The compound of claim 1 which is 7-chloro-4-[2-(4-methyl-benzylamino)]-ethoxy]-1,3-dihydro-indol-2-one or a pharmaceutically acceptable salt thereof.

9. The compound of claim 1 which is 4-[2-(N-benzyl-N-methyl-amino)-ethoxy]-7-chloro-1,3-dihydro-indol-2-one or a pharmaceutically acceptable salt thereof.

10. The compound of claim 1 which is 4-(2-butylamino-ethoxy)-7-chloro-1,3-dihydro-indol-2-one or a pharmaceutically acceptable salt thereof.

11. The compound of claim 1 which is 7-chloro-4-[2-(3,4-dihydro-1H-isoquinolin-2-yl)-ethoxy]-1,3-dihydro-indol-2-one or a pharmaceutically acceptable salt thereof.

12. The compound of claim 1 which is 7-chloro-4-[2-(1,3-dihydro-isoindol-2-yl)-ethoxy]-1,3-dihydro-indol-2-one or a pharmaceutically acceptable salt thereof.

13. The compound of claim 1 which is 4-{2-[(biphenyl-4-ylmethyl)-amino]-ethoxy}-7-chloro-1,3-dihydro-indol-2-one or a pharmaceutically acceptable salt thereof.

14. The compound of claim 1 which is 7-chloro-4-{2-[(napthalen-2-ylmethyl)-amino-ethoxy-1,3-dihydro-indol-2-one or a pharmaceutically acceptable salt thereof.

15. The compound of claim 1 which is 4-2-[4-phenyl-butylamino)-ethoxy]-1,3-dihydro-indol-2-one or a pharmaceutically acceptable salt thereof.

16. The compound of claim 1 which is 4-(2-benzylamino-ethoxy)-7-chloro-1,3-dihydro-indol-2-one or a pharmaceutically acceptable salt thereof.

17. The compound of claim 1 which is 4-(2-benzylamino-ethoxy)-7-fluoro-1,3-dihydro-indol-2-one or a pharmaceutically acceptable salt thereof.

18. The compound of claim 1 which is 4-[2-(cyclohexylmethyl-amino)-ethoxy)-7-fluoro-1,3-dihydro-indol-2-one or a pharmaceutically acceptable salt thereof.

19. The compound of claim 1 which is 4-{2-[(biphenyl-3-ylmethyl)-amino]-ethoxy}-7-fluoro-1,3-dihydro-indol-2-one or a pharmaceutically acceptable salt thereof.

20. The compound of claim 1 which is 4-{2-[3-(1H-Indol-yl)-propylamino]-ethoxy}-7-fluoro-3-thiomethyl-1,3-dihydro-indol-2-one or a pharmaceutically acceptable salt thereof.

21. The compound of claim 1 which is 4-[2-(1,3-dihydro-isoindol-2-yl)-ethoxy]-7-fluoro-1,3-dihydro-indol-2-one or a pharmaceutically acceptable salt thereof.

22. The compound of claim 1 which is 4-{2-[(biphenyl-4-ylmethyl)-amino]-ethoxy}-7-fluoro-1,3-dihydro-indol-2-one or a pharmaceutically acceptable salt thereof.

23. The compound of claim 1 which is 7-fluoro-4-{2-[(napthalen-2-ylmethyl)-amino]-ethoxy}-1,3-dihydro-indol-2-one or a pharmaceutically acceptable salt thereof.

24. The compound of claim 1 which is 4-[2-(3,4-dihydro-1H-isoquinolin-2-yl)-ethoxy]-7-fluoro-1,3-dihydro-indol-2-one or a pharmaceutically acceptable salt thereof.

25. The compound of claim 1 which is 4-(2-amino-ethoxy)-7-fluoro-1,3-dihydro-indol-2-one or a pharmaceutically acceptable salt thereof.

26. The compound of claim 1 which is bis-[2-(7-fluoro-1,3-dihydro-indol-2-one-4-yl)-ethoxy]-amine or a pharmaceutically acceptable salt thereof.

27. The compound of claim 1 which is 4-[2-(benzyl-methyl-amino)-ethoxy]-1,3-dihydro-indol-2-one or a pharmaceutically acceptable salt thereof.

28. The compound of claim 1 which is 4-{2-[bis-(3-methyl-benzyl)-amino]-ethoxy}-1,3-dihydro-indol-2-one or a pharmaceutically acceptable salt thereof.

29. The compound of claim 1 which is 4-(2-{[4-(4-fluoro-phenyl)-4-oxo-butyl]-methyl-amino}-ethoxy)-1,3-dihydro-indol-2-one or a pharmaceutically acceptable salt thereof.

30. A pharmaceutical composition of matter comprising a compound of the formula:

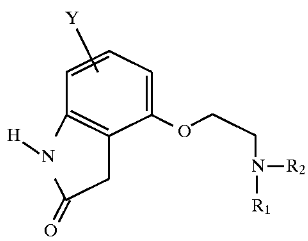

in which:

Y is hydrogen, halogen or alkoxy of 1 to 6 carbon atoms;

$R_1$ is hydrogen, alkyl of 1 to 6 carbon atoms or arylalkyl of 7 to 12 carbon atoms;

$R_2$ is hydrogen, alkyl of 1 to 6 carbon atoms or $—(CH_2)_nX_pAr$, where

X is oxygen or carbonyl;

Ar is cycloalkyl of 5 to 7 carbon atoms, aryl of 6 to 12 carbon atoms, haloaryl of 6 to 12 carbon atoms or arylaryl of 12 to 16 carbon atoms, oxindolyl, benzimidazolyl, indolyl, 2-oxobenzimidazolyl or 2-thioxobenzimidazolyl;

or $R_1$ and $R_2$, taken together with the nitrogen atom to which they are attached, complete a 3,4-dihydro-1H-isoquinolinyl or 1,3-dihydro-isoindolyl moiety;

n is one of the integers 1,2,3,4,5 or 6;

p is one of the integers 0 or 1;

or a pharmaceutically acceptable salt thereof and a pharmaceutically acceptable carrier therefor.

31. A method for reducing dopamine synthesis and release in a patient suffering from hyperactivity of the dopaminergic systems, which comprises administering to said patient a compound of the formula:

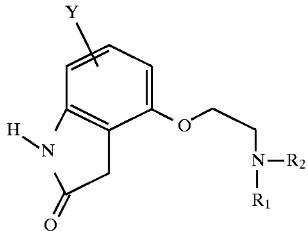

in which:

Y is hydrogen, halogen or alkoxy of 1 to 6 carbon atoms;

$R_1$ is hydrogen, alkyl of 1 to 6 carbon atoms or arylalkyl of 7 to 12 carbon atoms;

$R_2$ is hydrogen, alkyl of 1 to 6 carbon atoms or $—(CH_2)_nX_pAr$, where

X is oxygen or carbonyl;

Ar is cycloalkyl of 5 to 7 carbon atoms, aryl of 6 to 12 carbon atoms, haloaryl of 6 to 12 carbon atoms or arylaryl of 12 to 16 carbon atoms, oxindolyl, benzimidazolyl, indolyl, 2-oxobenzimidazolyl or 2-thioxobenzimidazolyl;

or $R_1$ and $R_2$, taken together with the nitrogen atom to which they are attached, complete a 3,4-dihydro-1H-isoquinolinyl or 1,3-dihydro-isoindolyl moiety;

n is one of the integers 1,2,3,4,5 or 6;

p is one of the integers 0 or 1;

or a pharmaceutically acceptable salt thereof, in an amount sufficient to modulate the dopamine systems of the brain.

32. A method for treating schizophrenia which comprises administering to a patient suffering from schizophrenia, orally or parenterally, a compound of the formula:

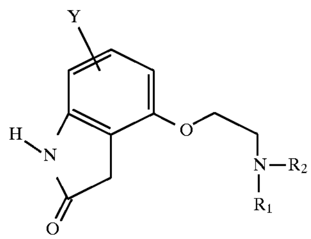

I in which:

Y is hydrogen, halogen or alkoxy of 1 to 6 carbon atoms;

$R_1$ is hydrogen, alkyl of 1 to 6 carbon atoms or arylalkyl of 7 to 12 carbon atoms;

$R_2$ is hydrogen, alkyl of 1 to 6 carbon atoms or —$(CH_2)_nX_pAr$, where

X is oxygen or carbonyl;

Ar is cycloalkyl of 5 to 7 carbon atoms, aryl of 6 to 12 carbon atoms, haloaryl of 6 to 12 carbon atoms or arylaryl of 12 to 16 carbon atoms, oxindolyl, benzimidazolyl, indolyl, 2-oxobenzimidazolyl or 2-thioxobenzimidazolyl;

or $R_1$ and $R_2$, taken together with the nitrogen atom to which they are attached, complete a 3,4-dihydro-1H-isoquinolinyl or 1,3-dihydro-isoindolyl moiety;

n is one of the integers 1,2,3,4,5 or 6;

p is one of the integers 0 or 1;

or a pharmaceutically acceptable salt thereof, in an amount sufficient to alleviate the symptoms of schizophrenia.

* * * * *